United States Patent [19]

Waddill: Harold G. et al.

[11] Patent Number: 5,422,042

[45] Date of Patent: Jun. 6, 1995

[54] IMIDAZOLIDONE POLYETHERAMINE STRENGTH ENHANCING ADDITIVES OF EPOXY RESIN SYSTEMS

[75] Inventors: Waddill: Harold G.; Wei-Yang Su; Michael Cuscurida; Terry L. Renken, all of Austin, Tex.

[73] Assignee: Huntsman Corporation, Salt Lake City, Utah

[21] Appl. No.: 154,764

[22] Filed: Nov. 19, 1993

[51] Int. Cl.$^6$ .............. C08G 59/40; C08G 59/62; C07D 233/04; C07D 233/32

[52] U.S. Cl. .............. 525/407; 525/504; 528/111; 528/367; 548/323.5

[58] Field of Search .............. 548/323.5; 525/407, 525/504; 528/111, 367

[56] References Cited

U.S. PATENT DOCUMENTS

| | | | |
|---|---|---|---|
| 3,347,926 | 10/1967 | Zech | 260/585 |
| 3,373,204 | 3/1968 | Hales et al. | 260/570.7 |
| 3,390,184 | 6/1968 | Moss et al. | 250/585 |
| 3,654,370 | 4/1972 | Yeakey | 260/584 B |
| 4,014,933 | 3/1977 | Boettger et al. | 260/563 R |
| 4,152,345 | 5/1979 | Gaudett et al. | 260/439 R |
| 4,153,581 | 5/1979 | Habermann | 252/472 |
| 4,409,399 | 10/1983 | Swift et al. | 564/473 |
| 4,420,606 | 12/1983 | Waddill | 525/504 |
| 4,766,245 | 8/1988 | Larkin et al. | 564/474 |
| 4,883,873 | 11/1989 | Abboud et al. | 548/324.1 |
| 4,973,761 | 11/1990 | Schoenleben et al. | 564/475 |
| 4,996,294 | 2/1991 | Cuscurida et al. | 528/421 |
| 5,003,107 | 3/1991 | Zimmerman et al. | 564/475 |
| 5,250,632 | 10/1993 | Waddill et al. | 525/407 |
| 5,288,873 | 2/1994 | Su et al. | 525/407 |

OTHER PUBLICATIONS

McLean et al., *Brit. Poly. J.*, 15, 66(1983).
Garton et al, *Poly. Eng. & Sci*, 27, No. 20, 1620(1987).
Grayson et al., ed., *Kirk–Othmer Encyclopedia of Chemical Technology*, Third Edition, vol. 7, p. 593.

*Primary Examiner*—Frederick Krass
*Attorney, Agent, or Firm*—Russell R. Stolle; Ron D. Brown

[57] ABSTRACT

This invention discloses the composition and preparation of imidazolidone modified polyetheramines. The alkyl polyetheramine is derived from 2-isopropylaminoethylamine and urea. N-isopropyl-2-imidazolidone is the intermediate product, which is alkoxylated and aminated to prepare the N-isopropyl imidazolidone polyetheramine. This invention also discloses the composition and preparation of oxazolidinone modified polyetheramines by reductive amination of polyols derived from 4-ethyl-4-hydroxymethyl-2-oxazolidone. The products of this invention have been tested in epoxy resin applications and improved properties have been demonstrated. These products may also be useful in polyurea applications.

6 Claims, No Drawings

IMIDAZOLIDONE POLYETHERAMINE STRENGTH ENHANCING ADDITIVES OF EPOXY RESIN SYSTEMS

BACKGROUND OF THE INVENTION

CROSS-REFERENCE

This application is related to U.S. application Ser. No. 07/928,583 now U.S. Pat. No. 5,250,637, to U.S. application Ser. No. 07/928,582, now U.S. Pat. No. 5,288,873, and to U.S. application Ser. No. 07/984,760, now U.S. Pat. No. 5,238,971.

1. Field of the Invention

The invention relates to novel epoxy curing compositions:

1.) an alkyl polyetheramine derived from imidazolidone(hereinafter referred to as IMD).
2.) aminated, alkoxylated derivatives of hydroxyalkyl-2-oxazolidinones.

These novel polyetheramines produce elastomers with good properties. The IMD derivative can be used in combination and the hydroxyalkyl-2-oxazolidinone derivative can be used alone or in combination with known polyalkyleneamine curing agents and reacted with multifunctional epoxy resins to produce systems which possess a level of flexibility and toughness not usually achieved. Due to the unique structure of these amines, which contain cyclic urea, cured systems show increased rigidity, are less extensible, and less resistant to impact than are systems cured with blends of other polyetheramines of equivalent weight.

These novel polyetheramines make it possible to prepare curing agents having a broad range of molecular weights, useful in a variety of epoxy, polyurea, and polyamide applications. The variety of possible combinations and molecular weights can result in a broad range of physical properties in cured products.

2. Related Art

Various strength enhancing additives for epoxy resin systems have been described. These additives, known as "fortifiers", differ considerably in structure from those of the proposed invention. See McLean, et. al., *Brit. Poly. J.*, 15, 66(1983); Garton. et. al., *Poly. Eng. & Sci.*, 27, No. 20, 1620(1987).

The amination of long alkoxylated alkyl chains terminated by hydroxyl groups is well-known in the art.

U.S. Pat. No. 3,654,370 to E. L. Yeakey teaches the amination of polyoxyalkylene polyols to form the corresponding amines by means of ammonia and hydrogen over a catalyst prepared by the reduction of a mixture of the oxides of nickel, copper and chromium. The amination is carried out at a temperature of 150° to 275° C. and 500 to 5000 psig.

U.S. Pat. No. 4,996,294 to Cuscurida et al. teaches a process in which an amine tetrol prepared by oxyalkylation of a propanediol with propylene oxide is catalytically aminated to provide, for example, an aminotetramine. The aminotetramines are useful for preparing polyurea products and as curing agents for epoxy resins.

A number of patents describe catalysts for producing primary or secondary amines. See, for example:
U.S. Pat. No. 4,766,245—(Raney Nickel) to Larkin & Renken; U.S. Pat. Nos. 4,152,345 & 4,153,581 to Habermann; U.S. Pat. No. 4,409,399 to H. E. Swift et al.; U.S. Pat. No. 3,390,184 to P. H. Moss et al.; U.S. Pat. No. 3,373,204 to R. A. Hales et al.; U.S. Pat. No. 3,347,926 to J. D. Zech; U.S. Pat. No. 4,014,933 to Boettger et al.; U.S. Pat. No. 4,973,761 to Schoenleben & Mueller; and U.S. Pat. No. 5,003,107 to Zimmerman & Larkin.

It is known in the art that compounds with primary and secondary amine functions can be used as reactive hardeners in epoxy resin formulations employed for protective coatings, electrical embodiments, adhesives, etc. Many of the known polyethyleneamines have been used for such applications. Grayson et al.,ed., *Kirk-Othmer Encyclopedia of Chemical Technology*, Third Edition, Vol. 7, p. 593.

SUMMARY OF THE INVENTION

The invention is a compound of the formula:

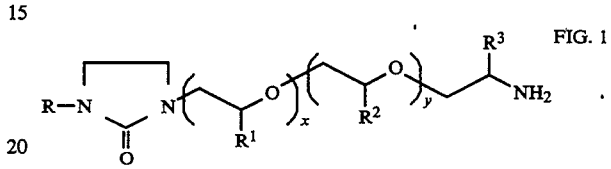

FIG. 1 wherein R is a linear or branched alkyl group of from about 1 to 6 carbon atoms, $R^1$, $R^2$ and $R^3$ are independently H or an alkyl group of from about 1 to 6 carbon atoms, and $x+y$ is from about 2 to 80.

Also disclosed is a compound of the formula:

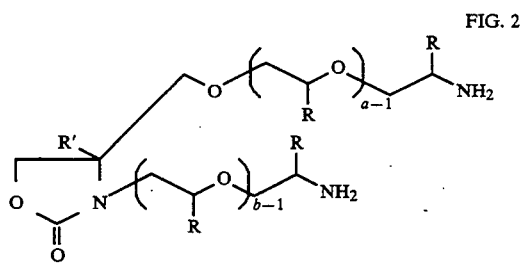

FIG. 2 wherein R is H or an alkyl group of from 1 to 16 carbon atom, R' is selected from the group consisting of hydrogen and lower alkyl radicals having about 1 to 8 carbon atoms and a $+b=n$ where n is the number of moles of alkylene oxide used in the alkoxylation step and has the range of 2 to 80.

This invention is also a process for the preparation of a polyetheramine containing an imidazolidone (cyclic urea) group which comprises continuously passing ammonia, hydrogen and the corresponding polyol over a catalyst comprising nickel in combination with a transition metal promoter selected from the group consisting of copper, chromium, molybdenum, manganese, iron and zinc, or mixtures thereof.

This invention is also an epoxy resin composition comprising a vicinal polyepoxide and a curing amount of the aminated alkoxylated derivative of the 1-alkyl-2-imidazolidone having the formula of FIG. 1. The resulting resin compositions produce materials having a degree of toughness and flexibility substantially improved over anything available in the art.

DESCRIPTION OF THE PREFERRED EMBODIMENTS

The sequence for preparing the novel imidazolidone containing polyetheramines (herein after referred to as IMD), starting with the substituted imidazolidone, is represented by the following:

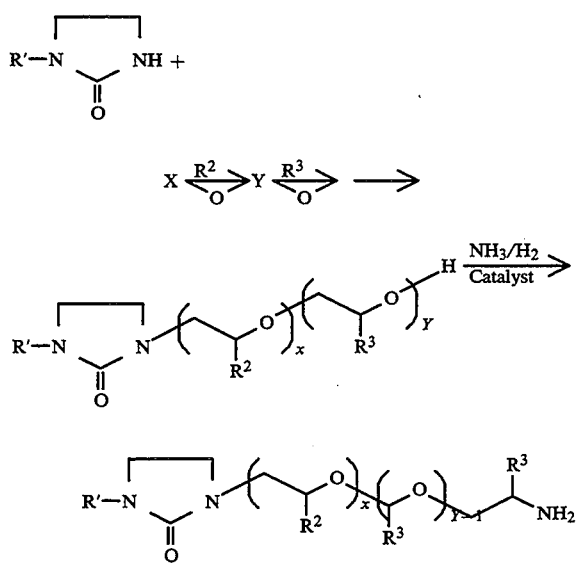

wherein R' is a linear or branched alkyl group of from about 1 to 6 carbon atoms, $R^2$ is H or an alkyl of about 1 to 16 carbon atoms, and $R^3$ is H or an alkyl group of from about 1 to 6 carbon atoms, and $x+y$ is from about 2 to 80.

The initiator, 1-alkyl-2-imidazolidone, can be easily prepared by reacting urea, dimethyl carbonate, ethylene carbonate or propylene carbonate with the corresponding 2-alkylaminoethylamine and is represented by the structure:

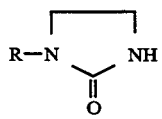

wherein R' is a linear or branched alkyl group of from about 1 to 6 carbon atoms.

The preferred initiator is N-isopropyl-2-imidazolidone and is represented by the formula:

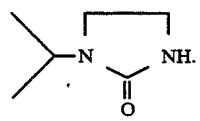

Also disclosed is a method for preparing the novel oxazolidinone containing polyetherdiamines, starting with the substituted oxazolidinone, and can be represented by the following:

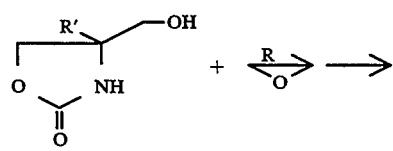

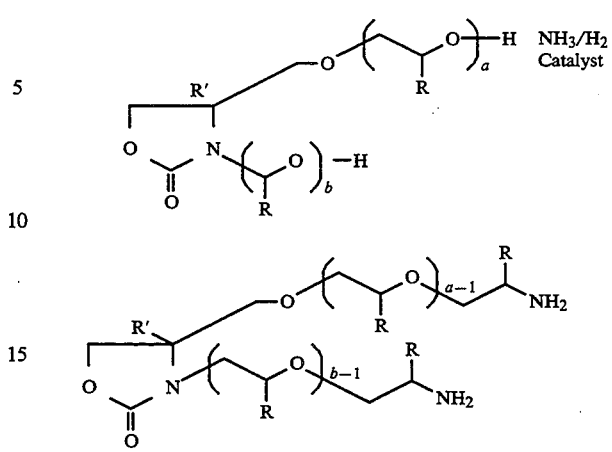

wherein R is H or an alkyl group of from 1 to 16 carbon atom, R' is selected from the group consisting of hydrogen and lower alkyl radicals having about 1 to 8 carbon atoms and $a+b=n$ where n is the number of moles of alkylene oxide used in the alkoxylation step and has the range of 2 to 80.

The initiator, hydroxyalkyl-2-oxazolidinone, can be easily prepared by reacting urea, dimethyl carbonate, ethylene carbonate or propylene carbonate with the corresponding 2-amino-2-alkyl-1,3-propandiol and is represented by the structure:

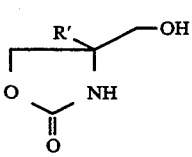

wherein R' is selected from the group comprised of hydrogen and lower alkyl radicals having from about 1 to 8 carbon atoms.

The alkoxylation reaction employed to prepare the propylene oxide adduct of both the cyclic urea initiator and the oxazolidinone initiator utilized to prepare the compounds of this invention is carried out according to methods well-known in the art, as described in Examples 2,3,13,14,15 and Tables 1 and 8.

The alkoxylation reactions proceed using alkylene oxides containing about 2 to 16 carbon atoms, or combinations thereof. Particularly suitable are ethylene oxide, propylene oxide, 1,2-butylene oxide and 2,3-butylene oxide or combinations thereof. Especially preferred alkylene oxides include propylene oxide and mixtures of propylene oxide and ethylene oxide. It can be noted from Tables 1 and 8 that variations in the number of moles of alkylene oxides or mixtures thereof used in alkoxylation result in predictably different hydroxyl number products, expressed as mg KOH/g, for tile resulting polyols which seems to likewise result in variations in the properties observed in the elastomers produced using tile novel polyetheramines.

The alkoxylated substituted IMD products and the alkoxylated substituted oxazolidinone-containing products can be converted to the corresponding primary amines by reaction with ammonia over a hydrogenation/dehydrogenation catalyst. Generally reductive amination catalysts are composed primarily of nickel, cobalt or copper, or these metals in combination as the active components. The catalyst can contain other metals as well, such as iron, zinc, chromium, manganese, zirconium, molybdenum, tungsten, rhenium, and ruthenium. Other promoters such as barium, magnesium, and phosphorous have been used as reductive amination catalysts. Precious metals such as platinum and palladium have also been used in some catalysts. The catalysts can be unsupported or supported. Common supports that have been used for these catalysts include alumina, silica, silica-alumina, zirconia, magnesia, and titania or mixtures thereof.

In the examples of reductive amination described herein the catalysts used comprised nickel alone or in combination with copper, chromium, and molybdenum unsupported or supported on alumina. The quantity of nickel, copper, chromium, and molybdenum which are employed in the catalyst may vary. Good results for tile IMD products are observed where the catalysts comprises about 30 to 80 wt % nickel, 5 to 15 wt % copper and 0.1 to 2 wt % each of chromium and/or molybdenum as well as at least 50 wt % of the refractory metal oxide support. One preferred catalyst composition comprises about 30 to 50 wt % nickel, about 5 to 10 wt % copper, about 1 to 2 wt % chromium, and about 0.1 to 1 wt % molybdenum and is deposited on an alumina support. Another preferred catalyst composition comprises about 70 to 80 wt % nickel, about 10 to 15 wt % copper, and about 1 to 2 wt % chromium. Good results for the oxazolidinone products are observed where the catalyst consisted essentially of 30 to 80 wt % nickel, 2 to 20 wt % copper and 0. 1 to 2 wt % each of chromium and molybdenum as well as at least 50 wt % of the refractory metal oxide support. A preferred composition comprises 70 to 80 wt % nickel, 10 to 20 wt % copper, and 0.5 to 1.5 wt % chromium. Another preferred composition comprises 35 to 40 wt % nickel, 4 to 8 wt % copper, 0.1 to 1.0 wt % molybdenum and is deposited on an alumina support.

It was observed that no significant amount of product degradation occurred during the amination reactions. A number of other catalysts known in the art to be active in reductive amination, such as Raney nickel, would be expected to be active and selective, and therefore, useful in this reaction.

The temperature for amination of the IMD polyol should be in the range of about 150° C. to 350° C. and is preferably from about 200° C. to 250° C. The pressure for amination should be in the range from about 500 to 4000 psig and preferably from about 1500 to 2500 psig.

The temperature for the amination of tile oxazolidinone polyol can range from about 150° C. to about 300° C. and from about 500 to about 4000 psig. The preferred temperature range is from about 200° to about 260° C. The preferred pressure range is from about 1000 to about 3000 psig.

Also disclosed is the use of compounds of the structure of FIG. 2 for making elastomers by reacting them with polyisocyantes using techniques known to those skilled in the art.

A wide variety of aromatic or aliphatic polyisocyanates may be used. Typical aromatic polyisocyanates include p-phenylene diisocyanate, polymethylene polyphenylisocyanate, 2,6-toluene diisocyanate, dianisidine diisocyanate, bitolylene diisocyanate, naphthalene-1,4-diisocyanate, bis(4-isocyanatophenyl)methane bis(3-methyl-3-isocyantophenyl)methane, bis(3-methyl-4-isocyanatophenyl)methane and 4,4'-diphenylpropane diisocyanate.

Other useful aromatic polyisocyanates are methylene-bridged polyphenyl polyisocyanate mixtures which have a functionality of from about 2 to about 4. See, for example, U.S. Pat. Nos. 2,683,730; 2,950,263; 3,012,008; 3,344,162 and 3,362,979.

In some applications a preferred polyaromatic polyisocyanate is methylene bis(4-phenylisocyanate) or MDI. Pure MDI, quasi-prepolymers of MDI, modified pure MDI, etc. Materials of this type may be used to prepare suitable RIM elastomers. Since pure MDI is a solid and, thus, often inconvenient to use, liquid products based on MDI are often used and are included in the scope of the terms MDI or methylene bis(4-phenylisocyanate) used herein. U.S. Pat. No. 3,394,164 is an example of a liquid MDI product. More generally uretonimine modified pure MDI is included also. This product is made by heating pure distilled MDI in the presence of a catalyst. The liquid product is a mixture of pure MDI and modified MDI:

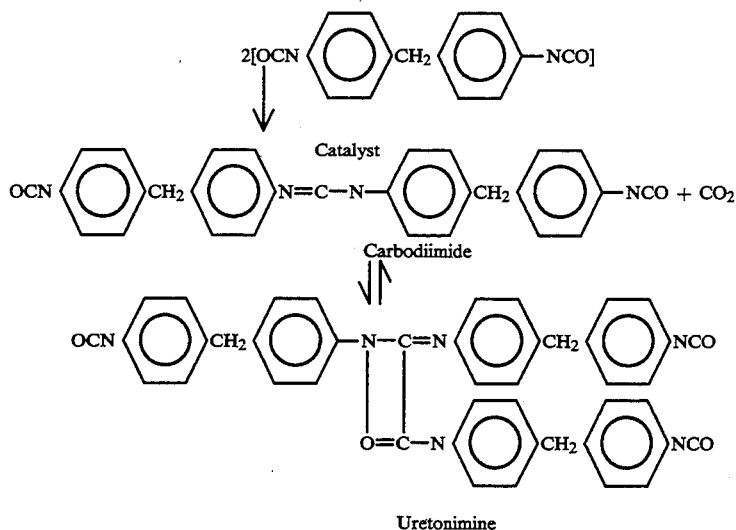

Uretonimine

Examples of a commercial material of this type are Dow's ISONATE® 125M (pure MDI) and ISONATE® 143L. Preferably, the amount of isocyanates used is the stoichiometric amount based on all the ingredients in the formulation.

In the instant invention it has been discovered that the aminated alkoxylated N-alkyl-2-imidazolidone derivatives having the structure identified in FIG. 1 and that the aminated hydroxyalkyl-2-oxazolidinone derivatives having the structure identified in FIG. 2 have properties which make them particularly valuable as curing agents for epoxy resins.

They can be used in epoxy resin compositions, such as films, castings, adhesives, etc., comprising a vicinal polyepoxide having an epoxide equivalency greater than about 1.8 and a curing amount of a curing agent such as the IMD amine or the oxazolidinone amine curing agents of this invention.

The level of toughness and flexibility developed in systems using the polyetheramine-containing curing agents of this invention has previously been difficult to obtain. The significant improvements are believed to be due in part to the unique structure of these compounds. Systems cured with the subject polyetheramines are substantially improved over those systems prepared with similar curatives which do not contain these structures.

The amines may be used as tile sole epoxy curative or blended with other known epoxy curatives to modify resin properties. These products may also be useful in epoxy, polyurea RIM and polyamide applications.

The compounds of this invention may be used as the sole epoxy curative or blended with other known curatives, such as, for example, polyoxyalkyleneamines to modify resin properties. Such polyoxyalkyleneamine include, but are not limited to, the polyoxyalkylenediamines of the JEFFAMINE® D-series as exemplified by tile structural formula:

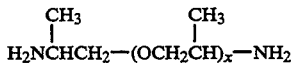

where x is a number from about 2 to 35 and includes, for example, JEFFAMINE® D-230, JEFFAMINE® D-400 and JEFFAMINE® D-2000.

The compounds of this invention may also be used in combination with a polyoxyalkylenediamine of the EDR-series represented by the formula:

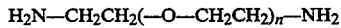

where n=2 or 3, represented by JEFFAMINE® EDR-148 or EDR-192.

Generally, the JEFFAMINE® polyoxyalkylenepolyamines employed in conjunction with the curing agents of this invention will have molecular weights of about 148 or more and, preferably will have molecular weights ranging from about 230 to 2000. All of the above JEFFAMINE® products are marketed by the Texaco Chemical Company, Houston, Tex.

The IMD-containing and the oxazolidinone-containing polyetheramines can be combined, not only with polyoxyalkyleneamines such as those of the JEFFAMINE® series mentioned above, but with a variety of commercially available amines. Suitable examples are ethyleneamines, including, but not limited to diethylenetriamines, triethylenetetramine, etc., and aromatic or cycloaliphatic amines and catalytic amines such as imidazoles.

Examples 6 to 11 compare properties of systems cured with the IMD-containing polyetheramine with properties of systems cured with JEFFAMINE® amines or blends of commercially available amines. The data confirms significant improvements in strength and flexibility.

Examples 20 and 21 (infra) compare properties of systems cured with the oxazolidinone-containing polyetherdiamine with properties of systems cured with either JEFFAMINE® D-400 or a blend of JEFFAMINE® D-400 and JEFFAMINE® D-2000.

In the instant invention, epoxy resin was cured at a temperature from about 70° C. to 90° C. for about 1 to 3 hours and subsequently cured at a temperature of from about 115° to 135° C. for about 4 to 5 hours for the IMD-containing compounds.

For the oxazolidinone-containing compounds curing of the epoxy resin can be carried out from about 60° to 150° C. for up to five hours and alternatively by curing at a temperature in the range of about 70° C. to 90° C. for about 1 to 3 hours and subsequently at a temperature of from about 110° C. to 130° C. for an additional period of about 2 to 4 hours.

The epoxy resins are preferably cured at a temperature above 70° C.

When the curing agent comprises a blend of the compounds of this invention and another polyoxyalkylenepolyamine, usually the polyetherdiamine will comprise from about 15 to about 100 wt % of the compound with the balance being the polyoxyalkylenepolyamine.

Generally, the amine-cured vicinal polyepoxide-containing compositions are organic materials having an average of at least 1.8 reactive 1,2-epoxy groups per. molecule. These polyepoxide materials can be monomeric or polymeric, saturated or unsaturated, aliphatic, cycloaliphatic, aromatic or heterocyclic, and may be substituted if desired with other substituents besides the epoxy groups, e.g., hydroxyl groups, ether radicals, aromatic halogen atoms and the like.

These vicinal polyepoxide-containing compounds typically are of an epoxy equivalent weight (EEW) of 150 to 250. Preferably the base resin, which has an epoxy equivalent weight of from 175 to 195, is derived from condensing epichlorohydrin with 4,4'-isopropylidenediphenol or 2,2-bis(p-hydroxyphenyl)propane to form 2,2-bis(p-2,3 epoxy propoxyphenyl)propane, a derivative of Bisphenol A.

Preferred polyepoxides are those of glycidyl ethers prepared by epoxidizing the corresponding allyl ethers or reacting, by known procedures, a molar excess of epichlorohydrin and an aromatic polyhydroxy compound; i.e., isopropylidene bisphenol, novolak, resorcinol, etc. The epoxy derivatives of ethylene or isopropylidene bisphenols are especially preferred.

A widely-used class of polyepoxides which are useful according to the instant invention includes the resinous epoxy polyethers obtained by reacting an epihalohydrin, such as epichlorohydrin, etc., with either a polyhydric phenol or a polyhydric alcohol. An illustrative, but by no means exhaustive, listing of suitable dihydric phenols includes 4,4'-isopropylidene bisphenol, 2,4'-dihydroxydiphenylethylmethane, 3,3'-dihydroxydiphenyldiethylmethane, 3,4'-diphenylmethylpropylmethane, etc.

Among the polyhydric alcohols which can be co-reacted with an epihalohydrin to provide these resinous epoxy polyethers are such compounds as ethylene glycol, propylene glycols, butylene glycols, pentane diols, bis(4-hydroxycyclohexyl)dimethylmethane, 1,4-dimethylolbenzene, glycerol, 1,2,6-hexanetriol, trimethylolpropane, mannitol, sorbitol, erythritol, pentaerythritol, their dimers, trimers and higher polymers, e.g., polyethylene glycols, polypropylene glycols, triglycerol, dipentaerythritol and the like, polyallyl alcohol, polyhydric thioethers, etc.

An epoxy resin which may be cured by the process of this invention is one prepared, for example, by the reaction of Bisphenol A with epichlorohydrin in the presence of sodium hydroxide. After condensation is complete, the crude resin is freed of residual epichlorohydrin, washed well to remove salt and soluble by-products and recovered. Among those which have been employed to demonstrate the effectiveness of the instant invention are diglycidyl ethers of Bisphenol A, such as liquid epoxy resin which has a molecular weight of approximately 380, a functionality of approximately 2, and an equivalent weight of approximately 185 to 192.

Optionally, the epoxy resin formulations of the instant invention can include an "accelerator" to speed the amine cure of the epoxy resin, especially at ambient temperatures. In several applications, such acceleration is beneficial, especially when an epoxy resin is used as an adhesive in a flammable environment, thus making elevated temperature cure inconvenient or even hazardous. Lee, H. and Neville, K., HANDBOOK OF EPOXY RESINS, pp. 7–14, describes the use of certain amine-containing compounds as epoxy curing agent accelerators.

Many accelerators are known in the art which can be utilized in accordance with the instant invention. Examples include salts of phenols, salicylic acids, amine salts of fatty acids, such as those disclosed in U.S. Pat. No. 2,681,901, and tertiary amines such as those disclosed in U.S. Pat. No. 2,839,480, incorporated herein by reference.

It will further be realized that various conveniently employed additives can be admixed with the polyepoxide-containing composition of the instant invention prior to final cure. For example, in certain instances it may be desirable to add minor amounts of hardeners along with various other accelerators and curing agent systems well-known in the art. Additionally, conventional pigments, dyes, fillers, flame-retarding agents and the like which are compatible and natural or synthetic resins can be added.

The preparation of a cured epoxy resin is carried out in the following manner:

Epoxy resin is normally used without dilution and without other additives.

A solvent may be used where components are very viscous.

To a component containing the epoxy resin is added an equivalent amount of either the IMD-containing polyetheramine or the oxazolidinone-containing polyetheramine alone or in combination with a polyoxyalkylenediamine. The mixture is then mixed, degassed and poured into molds. These blends, where mixed with other amine curatives, should be present in the epoxy resin in an amount sufficient to provide about 0.8 to 1.2 amino ($NH_2$) groups per oxirane group of the epoxy resin.

In the various Examples the following terms are used to describe properties measured:

HDT—(ASTM D648-72) Heat distortion temperature is the temperature at which a polymer sample distorts under load upon heating under specified conditions. HDTs can also be used to indicate the degree of cross-linking or extent of cure of an epoxy resin.

Shore D hardness—(ASTM D-2240-81) Measured at 0 and at 10 seconds indentation hardness with durometer.

Izod impact strength (ft-lb/in) (ASTM D256-81)—Izod impact testing is carried out with the pendulum-type device where the test specimen is positioned as a cantilever beam with the notched side facing the striker. Five samples are tested for impact with each formulation with the average being recorded as IZOD impact strength.

Tensile Strength, psi (ASTM D638-80)—The rupture strength (stress/strain product at break) per unit area of material subjected to a specified dynamic load. "Ultimate tensile strength" is the force, at break, when a sample is pulled apart.

Tensile Modulus, psi—Stress/strain

Flexural Strength, psi (ASTM D790-80)—A measure of the ability of a material to withstand failure due to bending.

$$\frac{\text{Flexural Modulus, psi}}{\text{Elongation at break, \%}} = \frac{\text{Stress (psi)}}{\text{Strain (in/in)}}$$

The following Examples are merely illustrative and should not be construed as limitations on the scope of the claims.

EXAMPLE 1

Reparation of N-Isopropyl-2-imidazolidone (6918-61)

A five-liter three necked flask equipped with a thermometer, condenser, stirrer, and nitrogen inlet was charged with 2-isopropylaminoethylamine (2550 g, 25 moles) and urea (1500 g, 25 moles). The reaction mixture was heated to 125° C. for seven hours and then 170° C. until no more gas releasing was observed. About 3155 g of N-isopropyl-2-imidazolidone was obtained. The reaction is represented as follows:

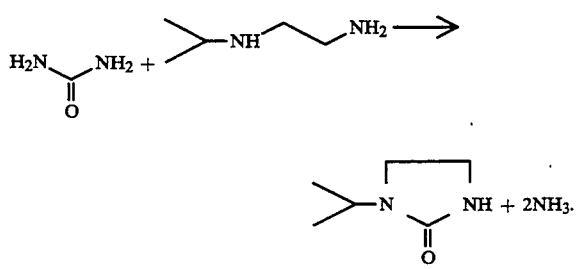

EXAMPLE 2-3

These examples will show the preparation of polyetheralcohol from N-isopropyl-2-imidazolidone (IPIMD). These products were prepared using the following reaction sequence:

IPIMD+3EO+2 PO→161 OH No. polyether alcohol

IPIMD+5PO →146 OH No. polyether alcohol

Reaction charges, details of preparation and properties of these products are given in Table 1.

TABLE 1

| SAMPLE NO. | 7045-15 | 7045-36 |
|---|---|---|
| Charge | | |
| IPIMD, lb. | 6.8 | 6.5 |
| Potassium Hydroxide, g[a] | 68.5 | 65.5 |
| Ethylene Oxide, lb. | 7.0 | — |
| Propylene Oxide, lb. | 6.16 | 14.7 |
| Magnesol 30/40, g[b] | 247 | 236 |
| Details of Preparation | | |
| Oxide Addition Time, hr. | 4 | 2 |
| Temperature, °C. | 105 | 115 |
| Pressure, psig, max. | 35 | 50 |
| Water Content Initiator, % | 0.05 | 0.07 |
| Properties | | |
| Hydroxyl No. mgKOH/g | 161 | 146 |
| Water, wt. % | 0.04 | 0.04 |
| pH in 10:6 Isopropanol-water | 10.7 | 11.24 |
| Sodium, ppm | 1.5 | 1.4 |
| Potassium, ppm | 3.5 | 2.8 |
| Viscosity, °F. cs | | |
| 77 | 133 | 197 |
| 100 | 80.3 | 80 |

[a] Added as 45% aqueous solution, direct to water content of less than 0.1% prior to oxide addition.
[b] Added as aqueous slurry.

EXAMPLE 4

Amination of 1-Isopropyl-2-imidazolidone + 3 EO + 2 PO (7045-15)

The polyol (7045-15, 2.87 meq/g total acetylatables), ammonia, and hydrogen were each continuously fed to a tubular reactor that was charged with 400 cc of a 1/25 inch extruded 38.5% Ni, 5.9% Cu, 1.1% Cr, and 0.6% Mo on alumina catalyst, at feed rates of 300 g/hr, 400 g/hr, and 28.1 l/hr at STP, respectively. The reactor pressure and temperature were maintained at 2000 psig and 235° C. The reactor effluent was stripped of ammonia, water, and other light materials. The stripped material contained 3.06 meq/g total acetylatables, 2.40 meq/g total amine and had a dull yellow-brown color.

Because the amine value of the product was lower than desired, it was further animated using 100 cc of ⅛ inch pellets of a 74% Ni, 12% Cu, and 1.5% Cr bulk metal catalyst in a smaller tubular reactor. The partially aminated product from the first amination, ammonia, and hydrogen were continuously fed to the reactor at rates of 80 g/hr, 120 g/hr, and 10 l/hr (at STP), and reactor pressure and temperature of 2000 psig and 235° C. The stripped product was analyzed to contain 2.97 meq/g total acetylatables, 2.83 meq/g total amine, and 2.82 meq/g primary amine. The color of the product was much lower than after the first amination.

EXAMPLE 5

Amination of 1-Isopropyl-2-imidazolidone + 5 PO (7045-36)

The polyol (7045-36, 2.60 meq/g total acetylatables), ammonia, and hydrogen were each continuously fed to a tubular reactor that was charged with 100 cc of the same ⅛ inch catalyst pellets of 74% Ni, 12% Cu, and 1.5% Cr mentioned in the previous experiment, at feed rates of 60 g/hr, 90 g/hr, and 7.5 l/hr (at STP). The reactor pressure and temperature were maintained at 2000 psig and 235° C. The material was stripped and the product (2 gallons) was analyzed to contain 2.80 meq/g total acetylatables, 2.60 meq/g total amine, and 2.57 meq/g primary amine.

EXAMPLE 6

Properties of Epoxy Resin System Cured with Triethylene tetramine(TETA) with an N-Isopropyl IMD Polyetheramine as Additive

TABLE 2

| Formulation: | 7014-22A | 7062-33B | 7062-33C | 7062-33D |
|---|---|---|---|---|
| Liquid epoxy resin[1] | 100 | 100 | 100 | 100 |
| Triethylenetetramine | 13 | 11.7 | 10.5 | 9.3 |
| N-Isopropyl IMD polyetheramine (6880-39-3)[2] | — | 10 | 20 | 30 |
| Strength Properties:[3] | | | | |
| Tensile strength, psi | 10700 | 7800 | 10800 | 10700 |
| Tensile modulus, psi | 405000 | 502000 | 496000 | 486000 |
| Elongation at break, % | 5.1 | 2.4 | 3.4 | 3.6 |
| Flexural strength, psi | 15700 | 19100 | 19950 | 19200 |
| Flexural modulus, psi | 402000 | 450000 | 486000 | 500000 |
| Adhesion Properties:[4] | | | | |
| Tensile Shear strength, psi | 2050 | 2500 | 3100 | 4050 |
| T-peal strength, pli. | 2.1 | 1.8 | 1.8 | 1.9 |

[1] Epoxy equivalent weight = 185–192
[2] Structure:

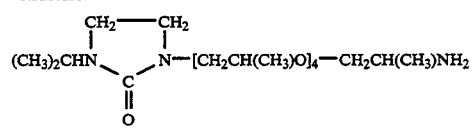

[3] ⅛ in casting, cured 2 hours at 80° C., 3 hours, 125° C.
[4] Bond: aluminum to aluminum; cured 1 hour at about 125° C.

EXAMPLE 7

Properties of Epoxy Resin System Cured with N-Aminoethyl piperazine(ALP) with an N-Isopropyl IMD Polyetheramine as Additive

TABLE 3

| Formulation: | 7062-34A | 7062-34B | 7062-34C | 7062-34D |
|---|---|---|---|---|
| Liquid epoxy resin[1] | 100 | 100 | 100 | 100 |
| N-Aminoethyl-piperazine | 23 | 22.1 | 21.0 | 18.8 |
| N-Isopropyl IMD polyetheramine (6880-39-3)[2] | — | 5 | 10 | 20 |
| Strength Properties:[3] | | | | |
| Tensile strength, psi | 9300 | 10000 | 10000 | 10200 |
| Tensile modulus, psi | 336000 | 350500 | 382000 | 432000 |
| Elongation at break, % | 6.8 | 10.6 | 8.4 | 7.2 |
| Flexural strength, psi | 14900 | 15800 | 16700 | 17400 |
| Flexural modulus, psi | 352000 | 384000 | 413000 | 456000 |
| Adhesion Properties:[4] | | | | |
| Tensile Shear strength, psi | 2600 | 3600 | 3300 | 4100 |
| T-peal strength, pli. | 2.2 | 2.5 | 2.5 | 2.6 |

[1] Epoxy equivalent weight = 185–192
[2] Structure:

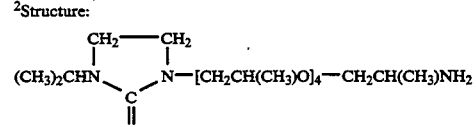

[3] ⅛ in casting, cured 2 hours at 80° C., 3 hours, 125° C.
[4] Bond: aluminum to aluminum; cured 1 hour at about 125° C.

EXAMPLE 8

Properties of Epoxy Resin System Cured with Jeffamine D-230 with an N-Isopropyl IMD Polyetheramine as Additive

TABLE 4

| Formulation: | 7014-72A | 7062-63A | 7062-63B | 7062-63C |
|---|---|---|---|---|
| Liquid epoxy resin[1] | 100 | 100 | 100 | 100 |
| Jeffamine D-230[5] | 33 | 30.9 | 29.3 | 26.2 |
| N-Isopropyl IMD polyetheramine (6880-39-3)[2] | — | 5 | 10 | 20 |
| Strength Properties:[3] | | | | |
| Tensile strength, psi | 9800 | 9600 | 9800 | 9800 |
| Tensile modulus, psi | 440000 | 463000 | 492500 | 512000 |
| Elongation at break, % | 6.8 | 7.5 | 6.2 | 6.0 |
| Flexural strength, psi | 17600 | 17000 | 17200 | 17300 |
| Flexural modulus, psi | 436000 | 439000 | 456000 | 479000 |
| Adhesion Properties:[4] | | | | |
| Tensile Shear strength, psi | 3900 | 3850 | 3400 | 3300 |
| T-peal strength, pli. | 2.2 | 3.2 | 3.6 | 3.1 |

[1] Epoxy equivalent weight = 185–192
[2] Structure:

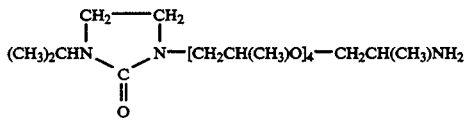

[3] ¼ in casting, cured 2 hours at 80° C., 3 hours, 125° C.
[4] Bond: aluminum to aluminum; cured 1 hour at about 125° C.
[5] Structure: $H_2NCH(CH_3)CH_2$—$[OCH_2CH(CH_3)]_x$—$NH_2$ where x = 2.6 and the amine hydrogen equivalent weight is about 60.

EXAMPLE 9

Properties of Epoxy Resin System Cured with Triethylenetetramine (TETA) with an N-Isopropyl IMD Polyetheramine as Additive

TABLE 5

| Formulation: | 7014-22A | 7062-39A | 7062-39B | 7062-39C | 7062-39D |
|---|---|---|---|---|---|
| Liquid epoxy resin[1] | 100 | 100 | 100 | 100 | 100 |
| Triethylene tetramine | 13 | 12.3 | 11.5 | 10.1 | 8.7 |
| N-Isopropyl IMD polyetheramine (6880-43-2)[2] | — | 5 | 10 | 20 | 30 |
| Strength Properties:[3] | | | | | |
| Tensile strength, psi | 10700 | 6300 | 7200 | 10200 | 11400 |
| Tensile modulus, psi | 405000 | 395000 | 442000 | 494000 | 517000 |
| Elongation at break, % | 5.1 | 1.8 | 2.4 | 3.0 | 4.9 |
| Flexural strength, psi | 15700 | 12200 | 15800 | 20000 | 19800 |
| Flexural modulus, psi | 402000 | 413000 | 461000 | 499000 | 507500 |
| Adhesion Properties:[4] | | | | | |
| Tensile Shear strength, psi | 2050 | 1700 | 2200 | 3000 | 2900 |
| T-peal strength, pli. | 2.1 | 1.7 | 1.6 | 1.9 | 1.8 |

[1] Epoxy equivalent weight 185–192
[2] Structure:

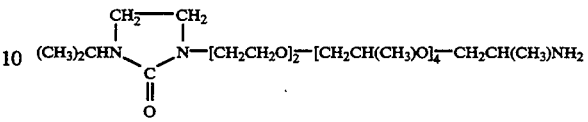

where the amine hydrogen equivalent weight is about 168.
[3] ¼ in casting, cured 2 hours at 80° C., 3 hours, 125° C.
[4] Bond: aluminum to aluminum; cured 1 hour at about 125° C.

EXAMPLE 10

Properties of Epoxy Resin System Cured with N-Aminoethylpiperazine (ALP) with an N-Isopropyl IMD Polyetheramine as Additive

TABLE 6

| Formulation: | 7062-34A | 7062-43A | 7062-43B | 7062-43C |
|---|---|---|---|---|
| Liquid epoxy resin[1] | 100 | 100 | 100 | 100 |
| N-Amino ethylpiperazine | 23.0 | 22.0 | 20.7 | 18.1 |
| N-Isopropyl IMD polyetheramine (6880-43-2)[2] | — | 5 | 10 | 20 |
| Strength Properties:[3] | | | | |
| Tensile strength, psi | 9300 | 10300 | 10500 | 9050 |
| Tensile modulus, psi | 336000 | 394000 | 428000 | 453000 |
| Elongation at break, % | 6.8 | 9.2 | 8.0 | 3.0 |
| Flexural strength, psi | 14900 | 16700 | 17300 | 18100 |
| Flexural modulus, psi | 352000 | 387000 | 415000 | 458000 |
| Adhesion Properties:[4] | | 7062-89A | 7062-89B | 7062-89C |
| Tensile Shear strength, psi | 2600 | 3600 | 3600 | 4000 |
| T-peal strength, pli. | 2.2 | 2.6 | 2.8 | 2.4 |

[1] Epoxy equivalent weight = 185–192
[2] Structure:

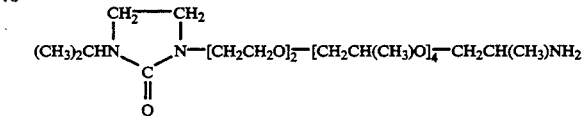

where the amine hydrogen equivalent weight is about 168.
[3] ¼ in casting, cured 2 hours at 80° C., 3 hours, 125° C.
[4] Bond: aluminum to aluminum; cured 1 hour at about 125° C.

EXAMPLE 11

Properties of Epoxy Resin System Cured with Jeffamine D-230 with an N-Isopropyl IMD Polyetheramine as Additive

TABLE 7

| Formulation: | 7014-72A | 7062-64A | 7062-64B | 7062-64C |
|---|---|---|---|---|
| Liquid epoxy resin[1] | 100 | 100 | 100 | 100 |
| Jeffamine D-230 | 33.0 | 30.6 | 28.9 | 25.3 |
| N-Isopropyl IMD polyetheramine (6880-43-2)[2] | — | 5 | 10 | 20 |
| Strength Properties:[3] | | | | |
| Tensile strength, psi | 9800 | 10200 | 10300 | 10400 |
| Tensile modulus, psi | 440000 | 442000 | 477000 | 500000 |
| Elongation at break, % | 6.8 | 5.8 | 5.4 | 4.6 |
| Flexural strength, psi | 17600 | 17600 | 18200 | 17900 |
| Flexural modulus, psi | 436000 | 447000 | 462000 | 475000 |
| Adhesion Properties:[4] | | | | |
| Tensile Shear strength, psi | 3900 | 3500 | 2600 | 3800 |

TABLE 7-continued

| Formulation: | 7014-72A | 7062-64A | 7062-64B | 7062-64C |
|---|---|---|---|---|
| T-peal strength, pli. | 2.2 | 2.0 | 2.1 | 1.8 |

[1]Epoxy equivalent weight = 185–192
[2]Structure:

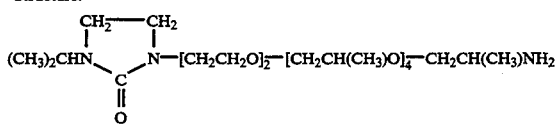

where the amine hydrogen equivalent weight is about 168.
[3] in casting, cured 2 hours at 80° C., 3 hours, 125° C.
[4]Bond: aluminum to aluminum; cured 1 hour at about 125° C.

Comments on Results Shown in Examples 6–11:

Two 1-alkyl IMD polyethermonoamines with slightly differing structure, i.e. one entirely from propylene oxide, the other from mixed ethylene and propylene oxides, were added in varying amounts to epoxy systems cured with three different but commonly used amine curatives. Strength and adhesion properties of formulations containing the IMD addition products were obtained and compared with systems containing no additive.

Surprisingly, results indicated that certain valuable properties were enhanced when even small amounts of the IMD product were added to the formulations. Tensile and flexural strengths were significantly increased with addition of small amounts of either of the IMD amines as were tensile and flexural moduli. With either triethylenetetramine(TETA) or N-aminoethylpiperazine(ALP), adhesive strength (tensile shear) was also considerably improved through inclusion of the additive. With Jeffamine D-230 as curative, no improvement in adhesive strength was noted with the additive but it should be noted that the tensile shear value obtained on curing with D-230 alone was much higher than was seen with either TETA or ALP. This high value was maintained with formulations containing added IMD monoamine but no improvement was shown.

Since the IMD monoamines were evaluated in a variety of epoxy resin systems with consistently improved properties, it should follow that similar results would be seen with other epoxy resin systems.

EXAMPLE 12 (6918-43)

Preparation of 4-ethyl-4-hydroxymethyl-2-oxazolidinone.

A two-liter three-necked flask equipped with a thermometer, condenser, stirrer, and nitrogen inlet was charged with 2-amino-2-ethyl- 1,3-propandiol(786g, 6.3 mole) and urea(380 g, 6.3 mole). The reaction mixture was heated to 125° C. for seven hours and then 170° C. until no more gas releasing was observed. About 929 g of product was obtained. The product was confirmed by NMR spectrum to be 4-ethyl-4-hydroxymethyl-2-oxazolidinone. The reaction may be depicted as follows:

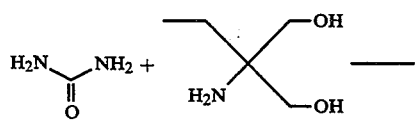

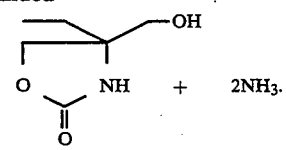

EXAMPLES 13–15

These examples will show the preparation of polyols from 4-ethyl-4-hydroxymethyl-2-oxazolidinone(EHMOXD). These products were prepared using the following reaction sequence:

| Products | Hydroxyl No., mg KOH/g |
|---|---|
| EHMOXD + 5 PO → | 263.0 |
| EHMOXD + 10 PO → | 173.0 |
| EHMOXD + 34.5 PO → | 64.1 |

Reaction charges, details of preparation and properties of these products are given in Table 8.

TABLE 8
PROPYLENE OXIDE ADDUCTS OF 4-ETHYL-4-HYDROXYL-2-OXAZOLIDINONE (EHMOXD)

| Sample No. | 6976-71 | 6910-98 | 6786-88 |
|---|---|---|---|
| Charge | | | |
| EHMOXD, lb. | 20 | 2 | — |
| 400 m.wt. PO adduct of EHMOXD, lb[a] | — | — | 12 |
| Potassium Hydroxide, g[b] | 90.7 | 40.3 | 241.9 |
| Propylene Oxide, lb | 48 | 8 | 48 |
| Magnesol 30/40, g[c] | 725 | 145 | 653 |
| Di-t-butyl p-Cresol, g | — | — | 13.6 |
| DETAILS OF PREPARATION | | | |
| Oxide addition time, hr. | 5.0 | 1.0 | 10.0 |
| Temperature, °C. | 110 | 115 | 110 |
| Pressure, psig, max. | 50 | 85 | 60 |
| Water Content Initiator, % | 0.05 | 0.03 | 0.2 |
| PROPERTIES | | | |
| Hydroxyl No. MgKOH/g | 263 | 173 | 64.1 |
| Water, wt. % | 0.05 | 0.06 | 0.03 |
| pH in 10:6 isopropanol-water | 12.0 | 11.5 | 9.4 |
| Sodium, ppm | 0.5 | 0.5 | 0.2 |
| Potassium, ppm | 3.0 | 3.3 | 1.2 |
| Viscosity, °F., cs | | | |
| 77 | 2275 | 671 | 683 |
| 100 | 661 | 247 | 276 |

EXAMPLE 16

Amination of Propoxylated(10 Mole PO) 4-Ethyl-4-Hydroxymethyl-2-Oxazolidinone (EHMOXD) 6910-98

The polyol used in this amination was 10 mole propylene oxide adduct of EHMOXD (NB 6910-98) and had a hydroxyl number of 173 mg KOH/g (3.24 meq/g). The amination was performed in a 100 cc tubular reactor fully charged with 72.2 g of a 1/25 inch extruded 38.5% Ni, 5.9% Cu, 1.1% Cr, and 0.6% Mo on gamma alumina catalyst. The polyol, ammonia, and hydrogen were each continuously fed to the heated reactor at 100 g/hr, 125 g/hr, and 9.35 l/hr (STP), respectively. The reactor temperature and pressure were maintained at 225° C. and 2000 psig.

Approximately one gallon of aminated reactor effluent was collected and stripped of ammonia, water, and other light materials. Wet chemical analyses indicated the material contained 3.26 meq/g total acetylatables, 3.105 meq/g total amine, 2.988 meq/g primary amine, and 0.26% water.

EXAMPLE 17

Amination of Propoxylated 4-Ethyl-4-Hydroxymethyl-2-Oxazolidinone(EH-MOXD) 6976-88

The polyol used in this amination was an approximately 2000 mw propoxylated EHMOXD (NB 6976-88) and had a hydroxyl number of 64 mg KOH/g (1.14 meq/g). The amination was performed in a 600 cc tubular reactor fully charged with a bulk metal Ni Catalyst (72% Ni, 12% Cu, 1% Cr) in the form of ⅛ inch diameter×⅛ length pellets. The polyol, ammonia, and hydrogen were each continuously fed to the heated reactor at 0.44 lb/hr, 0.66 lb/hr, and 19 l/hr (STP), respectively. The reactor temperature and pressure were maintained at 230° C. and 2000 psig. A sample of the reactor effluent was stripped of ammonia, lights, and water and then found to have a total amine content of 0.779 meq/g.

Light materials were vented from the reactor effluent at ambient conditions and this partially aminated material was fed to the reactor to achieve a higher level of amination. The partially aminated material, ammonia, and hydrogen were fed to the unit at rates of 0.44 lb/hr, 0.66 lb/hr, and 19 l/hr, respectively. The reactor temperature and pressure were maintained at 230° C. and 2000 psig. The reactor effluent was stripped of ammonia, lights, and water and then determined to contain 1.15 meq/g total acetylatables, 0.918 meq/g total amine, and 0.850 meq/g primary amine.

EXAMPLE 18

Amination of Propoxylated (5 Mole PO) 4-Ethyl-4-Hydroxymethyl-2-Oxazolidinone (EHMOXD) 6976-71

The polyol used in this amination was a five mole propylene oxide (PO) adduct of EHMOXD (NB 6976-71) and had a hydroxyl number of 263 mg KOH/g (4.69 meq/g). The amination was performed in a 100 cc tubular reactor fully charged with a bulk metal Ni catalyst (72% Ni, 12% Cu, 1% Cr) in the form of ⅛ inch diameter×⅛ length pellets. The polyol, ammonia, and hydrogen were each continuously ted to the heated reactor at 60 g/hr, 90 g/hr, and 7.5 l/hr (STP), respectively. The reactor temperature and pressure were maintained at 245° C. and 2000 psig. All five gallons of polyol were fed to the reactor and collected. Samples of the reactor effluent were stripped of ammonia, lights, and water and then analyzed by titration methods. A typical sample analyzed as 5.11 meq/g total acetylatables, 4.39 meq/g total amine, and 4.05 meq/g primary amine.

The reactor effluent from above was fed to the amination reactor at about the same reactor conditions as given above, except that a temperature of 235° C. was used. The partially aminated material was fed at a rate of 60 g/hr. The ammonia and hydrogen were fed to the unit at rates of 90 g/hr and 9.35 l/hr, respectively. The reactor effluent was collected in several one gallon samples. These were stripped of ammonia, lights, and water and then analyzed. A typical sample analyzed as 5.19 meq/g total acetylatables, 4.95 meq/g total amine, 4.55 meq/g primary amine, and 0.22 meq/g tertiary amine.

EXAMPLE 19 (7068-75) USAGE EXAMPLE

To a paper cup was added 40 g of the sample of Example 18 and 25.3 g of methylene bis(4-phenylisocyanate). After stirring with a tongue depressor, a tough elastomer was obtained.

EXAMPLE 20

Properties obtained by curing with an oxazolidinone-containing polyoxypropylenediamine were compared with those from a standard polyoxypropylenediamine of similar equivalent weight (Jeffamine D-400) in Table 9. These results indicate that the system cured with the oxazolidinone-containing polyetheramine was considerably stronger (i.e. higher strength, modulus values) more heat resistant (i.e. much higher HDT value) and tougher (i.e. greater elongation, higher impact value) than was the system cured with Jeffamine D-400. Thus, with amines of similar equivalent weight, the oxazolidinone-containing amine would be preferred.

TABLE 9

| Formulation (pbw) | 7062-71A | TCC Literature[4] |
|---|---|---|
| Liquid Epoxy resin[1] | 100 | 100 |
| Oxazolidinone-Containing Amine[2] | 60 | — |
| Polyoxypropylenediamine[3] | — | 60 |
| Properties: | | |
| Cured ⅛-in casting | | |
| Cured: 2 hours 80°, 3 Hours, 125° C. | | |
| Shore D hardness, 0–10 sec. | 86–83 | 74–70 |
| HDT, °C., 264 psi | 74.0 | 45.0 |
| Izod impact strength, ft.-lbs/in. | 1.65 | 0.86 |
| Tensile strength, psi | 9900 | 7400 |
| Tensile modulus, psi | 468000 | 385000 |
| Elongation at break, % | 6.6 | 4.5 |
| Flexural strength, psi | 17200 | 11600 |
| Flexural modulus, psi | 448000 | 434000 |
| % weight gain, 24-hour water boil | 3.4 | 2.8 |
| % weight gain, 3-hour acetone boil | 11.9 | 25.0 |

[1]Diglycidyl ether of Bisphenol A; epoxy equivalent weight 185–192.
[2]Structure:

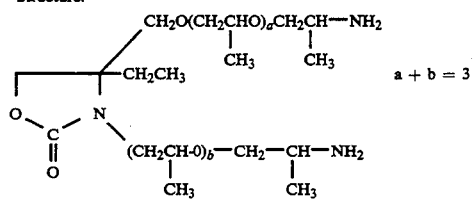

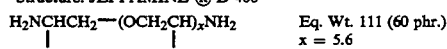

Eq. Wt. 111 (60 phr.)
x = 5.6

[4]Booklet: "JEFFAMINE ® Polyoxypropyleneamine Curing Agents for Epoxy Resins" Table V, Formulation D, p. 13.

EXAMPLE 21

Table 10 reveals a comparison of properties obtained on curing with a high molecular weight oxazolidinone-containing polyetheramine with those obtained with a blend of two standard polyetheramines of nearly identical equivalent weight (Jeffamine D-400/D-2000; no single commercial polyetheramine of like equivalent weight is available). The comparison indicates a similarity of results as shown in Example 20. A much stronger, less flexible system resulted from curing with the oxazolidinone-containing amine. It is remarkable that an amine of this molecular weight produced a cured epoxy resin system with the strength and modulus values shown. This behavior is further proof that the oxazolidinone structure has a definite effect (favorable) upon cured epoxide properties.

TABLE 10

| Formulation: | 7014-85A | 7128-11B |
|---|---|---|
| Liquid epoxy resin[1] | 100 | 100 |
| Oxazolidinone-containing amine[2] | 87 | — |
| Polyoxypropylenediamine blend[3] | — | 88 |
| Properties: | | |
| Cured ⅛-in. casting | | |
| Cured: 2 hours 80°, 3 hours 125° C. | | |
| Shore D hardness, 0-10 sec. | 80–78 | 57–34 |
| HDT, °C., 264 psi | 38.3 | <23 |
| Tensile strength, psi | 6800 | 1000 |
| Tensile modulus, psi | 388000 | 1700 |
| Elongation, % (at break) | 4.0 | 59.9 |
| Flexural strength, psi | 12500 | — |
| Flexural modulus, psi | 419000 | — |
| % Weight gain, 24-hour water boil | 2.9 | 2.7 |
| % Weight gain, 3-hour acetone boil | 36.6 | 42.3 |
| Adhesion Properties: | | |
| Cured: 1 hour, 125° C.[4] | | |
| Tensile shear strength, psi | 4200 | 1700 |
| T-peel strength, pli | 3.7 | 28.0 |

[1] Diglycidylether of Bisphenol A; epoxy equivalent weight 185–192.

[2] Structure:

$$\text{CH}_2\text{CH}_3 - \begin{array}{c} \text{CH}_2\text{O}(\text{CH}_2\text{CHO})_a\text{CH}_2\text{CH}-\text{NH}_2 \\ | \quad\quad\quad\quad | \\ \text{CH}_3 \quad\quad \text{CH}_3 \end{array}$$

$$\begin{array}{c} O \\ \| \\ O-C-N-(\text{CH}_2\text{CH-O})_b-\text{CH}_2-\text{CH}-\text{NH}_2 \\ \quad\quad | \quad\quad\quad | \\ \quad\quad \text{CH}_3 \quad\quad \text{CH}_3 \end{array}$$

$a + b = 8$

[3] Blend of 55% by weight of JEFFAMINE ® D-400 having the structure:

$$\text{H}_2\text{NCHCH}_2-(\text{OCH}_2\text{CH})_x\text{NH}_2 \qquad \text{Eq. Wt. 111 (60 phr.)}$$
$$\quad\; | \quad\quad\quad\quad\; | \qquad\qquad\qquad x = 5.6$$
$$\text{CH}_3 \quad\quad \text{CH}_3$$

and JEFFAMINE ® D-2000 with structure identical to JEFFAMINE ® D-400 except x = 33.1 of blend Eq. Wt. 163(88 phr.).

[4] Bond: acid etched aluminum to aluminum bond.

We claim:

1. A compound of the formula:

$$R-N\underset{\underset{O}{\|}}{\overset{\phantom{|}}{\diagdown}}N-(\text{CH}_2\text{CHO})_x(\text{CH}_2\text{CHO})_y\text{CH}_2\overset{R^3}{\underset{|}{\text{C}}}\text{HNH}_2$$
$$\quad\quad\quad\quad\quad\quad | \quad\quad\quad | \\ \quad\quad\quad\quad\quad\quad R^1 \quad\quad\; R^2$$

wherein R is a linear or branched alkyl group of from about 1 to 6 carbon atoms, $R^1$, $R^2$ and $R^3$ are independently H or an alkyl group of from about 1 to 6 carbon atoms, and $x+y$ is from about 2 to 80.

2. The compound of claim 1 wherein R is an isopropyl group, $x=4$, $y=0$ and $R^1$ and $R^3$ are both a methyl group.

3. The compound of claim 1 wherein R is an isopropyl group, $x=2$, $y=2$, $R^1=H$ and $R^2$ and $R^3$ are both a methyl group.

4. An epoxy resin composition comprising:
   a) A vicinal polyepoxide, and
   b) a curing amount of the aminated alkoxylated derivative of $$R-N\underset{\underset{O}{\|}}{\overset{\phantom{|}}{\diagdown}}N-(\text{CH}_2\text{CHO})_x(\text{CH}_2\text{CHO})_y\text{CH}_2\overset{R^3}{\underset{|}{\text{C}}}\text{HNH}_2$$
$$\quad\quad\quad\quad\quad\quad | \quad\quad\quad | \\ \quad\quad\quad\quad\quad\quad R^1 \quad\quad\; R^2$$

wherein R is a linear or branched alkyl group of from about 1 to 6 carbon atoms, $R^1$, $R^2$ and $R^3$ are independently H or an alkyl group of from about 1 to 6 carbon atoms, and $x+y$ is from about 2 to 80.

5. The composition of claim 4, cured at a temperature from about 70° C. to 90° C. for about 1 to 3 hours and subsequently cured at a temperature of from about 115° to 135° C. for about 4 to 5 hours.

6. The composition of claim 4, cured at a temperature above 70° C.

* * * * *